United States Patent [19]

Tomiyama et al.

[11] Patent Number: 4,631,292
[45] Date of Patent: Dec. 23, 1986

[54] 1,3-DIOXANE DERIVATIVES, METHOD OF THEIR SYNTHESIS AND ANTI-PEPTIC ULCER AGENT

[75] Inventors: Tsuyoshi Tomiyama, Sakaki; Akira Tomiyama, Togura, both of Japan

[73] Assignee: Kotobuki Seiyaku Co., Ltd., Nagano, Japan

[21] Appl. No.: 636,143

[22] Filed: Jul. 31, 1984

[30] Foreign Application Priority Data

Aug. 8, 1983 [JP] Japan ................. 58-144709

[51] Int. Cl.$^4$ .......................... C07D 319/06
[52] U.S. Cl. .................... 514/452; 514/925
[58] Field of Search ............ 549/369, 333; 424/278; 514/452, 925

[56] References Cited

U.S. PATENT DOCUMENTS

| | | | |
|---|---|---|---|
| 2,691,026 | 10/1954 | Harvey | 549/333 |
| 3,010,945 | 11/1961 | Ikeda | 549/369 |
| 3,423,430 | 1/1969 | Cahn et al. | 549/369 |
| 4,003,918 | 1/1977 | Hughes | 549/369 |
| 4,085,222 | 4/1978 | Rhodes et al. | 514/452 |
| 4,105,677 | 8/1978 | Taylor | 549/369 |

FOREIGN PATENT DOCUMENTS

| | | | |
|---|---|---|---|
| 0039029 | 11/1981 | European Pat. Off. | 549/369 |
| 0138540 | 4/1985 | European Pat. Off. | 514/925 |
| 2334378 | 1/1975 | Fed. Rep. of Germany | 549/369 |
| 3017540 | 11/1981 | Fed. Rep. of Germany | 549/333 |
| 948084 | 1/1964 | United Kingdom | 549/369 |
| 411086 | 1/1974 | U.S.S.R. | 549/333 |
| 0688501 | 11/1979 | U.S.S.R. | 549/369 |

OTHER PUBLICATIONS

Nikol'skaya et al, Chem. Abstracts, 89:109295p (1978).

Primary Examiner—Ethel G. Love
Attorney, Agent, or Firm—Robert E. Burns; Emmanuel J. Lobato; Bruce L. Adams

[57] ABSTRACT

A series of new 1,3-dioxane derivatives are disclosed. These compounds have an outstanding anti-peptic ulcerative activity and are useful as novel anti-peptic ulcer agents. Such compounds are synthesized by reacting a 1,3-butanediol derivative with suitable ketone.

7 Claims, No Drawings

1,3-DIOXANE DERIVATIVES, METHOD OF THEIR SYNTHESIS AND ANTI-PEPTIC ULCER AGENT

SUMMARY OF THE INVENTION

The principal object of the present invention is the provision of a novel anti-peptic ulcer agent.

Another important object of the present invention is the provision of a novel compound having advantageous pharmaceutical properties.

Still another object of the present invention is the provision of a pharmaceutical composition useful as an anti-peptic ulcerative agent.

Further important object of the present invention is the provision of a method of preparing an oral medicine of chemical stability containing a novel compound of the present invention.

These and other objects of the invention will become apparent from the detailed description set forth below.

DETAILED DESCRIPTION OF THE INVENTION

This invention relates to novel 1,3-dioxane derivatives, a method of their synthesis and their use for potent anti-peptic ulcer agents.

The compounds of the invention are represented by the general formula (I):

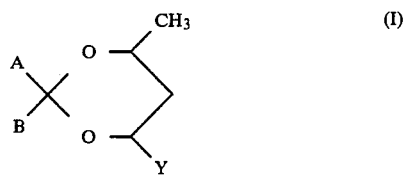

(I)

wherein A is an alkyl, alkenyl or

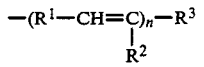

group in which $R^1$ is alkylene, $R^2$ and $R^3$ are hydrogen or a lower alkyl group and n is 1-4, and B and Y each represents hydrogen or a lower alkyl group. Also the compounds of the invention include the general formula Ia in which A and B in the formula I form a cyclic group:

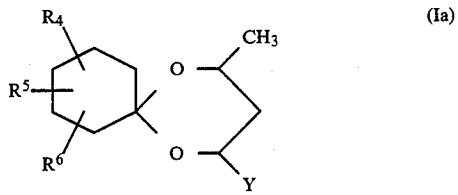

(Ia)

wherein $R^4$, $R^5$ and $R^6$ each represents hydrogen or lower alkyl groups

In the general formula I, A may also be a branched alkyl or alkenyl group consisting of 3-15 carbon atoms.

The compounds included in the formula I and Ia are as follows.

(1) 2-(4-methyl-3-pentene)-6-methyl-1,3-dioxane
2-(2,6-dimethyl-5-heptene)-6-methyl-1,3-dioxane
(3) 2-(n-nonyl)-6-methyl-1,3-dioxane
(4) 2-(trans-1-pentenyl)-6-methyl-1,3-dioxane
(5) 2-(4-methyl-3-pentenyl)-2-methyl-4-methyl-1,3-dioxane
(6) spiro[2isopropyl-5-methyl-cyclohexane-1,2'-4'-methyl 1',3']dioxane
(7) 2-(4,8-dimethyl-3,7-nonadiene)-6-methyl-1,3-dioxane
(8) 2-(4,8,12-trimethyl-3,7,11-dodecatriene)-2-methyl-6-methyl-1,3-dioxane
(9) 2-(4-methyl-3-pentene)-4,6-dimethyl-1,3-dioxane
(10) 2-(2,6-dimethyl-5-heptene)-4,6-dimethyl-1,3-dioxane
(11) 2-(4-methyl-3-pentenyl)-2-methyl-4,6-dimethyl-1,3-dioxane
(12) 2-(4,8-dimethyl-3,7-nonadiene)-2-methyl-4,6-dimethyl-1,3-dioxane
(13) 2-(4,8,12-trimethyl-3,7,11-tridecatriene)-2-methyl-4,6-dimethyl-1,3-dioxane
(14) 2-(4,8,12,16-tetramethyl-3,7,11,15-heptadecatetraene)-2-methyl-4-methyl-1,3-dioxane
(15) 2-(4-methyl-3-pentenyl)-2-ethyl-4-methyl-1,3-dioxane The above-mentioned compounds numbered from 1 to 15, will be refered to hereinafter, as Compound 1, Compound 2, . . . , Compound 15, respectively.

The compounds of the invention are prepared as follows.

A compound shown by the formula (II)

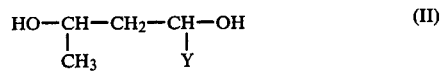

(II)

wherein the symbols are the same as above mentioned is reacted with a compound of the formula(III)

(III)

Particularly, for compounds of the general formula Ia, a compound of formula IIIa is changed to one of the formula III. For example, the compounds expressed in the formula III are as follows, citronellal, decyl aldehyde, trans-2-hexanal, cis-2-hexanal, 5-methyl-4-hexanal, 6-methyl-2-heptenone, geranyl acetone, L-mentone.

The ratio of the compound II to the compound II or IIIa for their reaction is selected from the range of 0.5-10.

As acid catalyzers, both organic and inorganic acids can be employed. Examples of inorganic acid are phosphoric, sulfonic and hydrochloric acids. Examples of organic acid are p-toluenesulfonic acid, benzenesulfonic acid, acetic acid and propionic acid.

The solvents used in this case are for example benzene, toluene and xylene which are inert in reaction.

Preferably, $H_2O$ generated during reaction should be removed. For this purpose, such compounds as $MgSO_4$, $Na_2SO_4$ or a molecular-sieve are used, if they are to be used in combination.

The temperature of reaction ranges from 90° to 150° C. The reaction mixture is washed with water to remove the catalyzer, and extracted with an organic solvent.

After removal of the solvent, the product is purified by disillation under reduced pressure or by column chromatography.

Recently, it has been reported that Anthemis nobilis contains 1,3-butanediol, isobutyric acid or angelic acid ester. Based on this information, the anti-peptic ulcer activities of these novel 1,3-dioxane derivatives were examined and found to have potent activities.

For pharmaceutical purposes, the compounds of the present invention are administered perorally or parenterally. In the case of oral administration, the compound of the invention can be used as it is or with suitable pharmaceutically inert carriers, in the form of tablets, capsules, powder or granules. For parenteral use, the compound is dissolved in vegetable oil in the form of a solution, emulsion and suspension.

Above all, since, in the general formula (I) of the compounds of the present invention, wherein when A is $-CH_2CH_2CH=C(CH_3)_2$, B is H, $CH_3$ or $C_2H_5$ and Y is H or $CH_3$, compound 5 and its similar derivatives, that is, compound 1, compound 9 and compound 15 are liquid materials, in the case of using them as oral medicines for clinical purposes, except in the form of capsules filled with the compound in liquid form, they cannot be administered as they are. Therefore, in order to use these compounds in the form of powder or granules they must be absorbed in an excipient which can be accepted by the authorized concern for manufacturing pharmaceuticals and pulverized.

However, when pulverizing compound 5 and its similar derivatives with an excipient in common use, the powder thus produced tends to be decomposed with the time. Due to this aging the manufacture them into pharmaceuticals in solid form has become rather difficult, since it is important to ensure that stable compounds are produced. The inventors of the present invention attempted various researches. As the result they have discovered that when compound 5 and its similar derivatives were pulverized using an excipient rendered alkaline with a base beforehand, there occurred no decomposition with time of the product thus treated due to aging. Certainly under these circumstances, the present invention has been completed with success.

The method of preparing oral medicine containing compound 5 or its similar derivatives consists in preparing medicines by pulverizing compound 5 and its similar derivatives in the usual manner using a basic excipient which has been obtained by making excipients in common use basic, for example, such excipients as synthesized aluminum silicate, avicel, neusilin, alcamac, syloid, β-cyclodextrin, and L-glutamine used either alone, respectively, or a suitable mixture thereof is made basic with a basic material with medical authorization for use, for example, a basic amino acid or inorganic base.

As the aforesaid basic amino acids, lysine and arginine can be exemplified. At the same time, as inorganic salts with medical authorization for use, for example, $NaHCO_3$, $Na_2CO_3$, $NaOH$, $KOH$, $KHCO_3$ and $K_2CO_3$ can be exemplified.

As preferred embodiments of the aforesaid basic treatment, in the case of basic amino acids, there is shown a method of mixing an excipient evenly with the aforesaid amino acid so that the content of said amino acid is 5–50% or thereabouts, depending on the properties of the excipient in use or in the case of using an inorganic base, there is shown a method of preparing a suitable solution, for example, an aqueous solution of 0.05–0.5N of said inorganic base, adding this solution to a suitable excipient for use and after adjusting pH of the resulting solution to more than 8, drying the excipient thus treated. The oral medicine containing compound 5 or its similar derivative produced by the method of the present invention shows almost no decomposition with time due to aging, nor does it lose its medical effectiveness.

Table 1 shows certain results in percentage of remaining compound 5 measured immediately after manufacture and one week after manufacture concerning the oral medicines 1–5, which were obtained in the working examples described hereinafter.

In the working example 1 dealing with a control, there is shown the percentage of remaining compound 5 using synthesized aluminum silicate without the treatment of L-arginine.

TABLE 1

| No. of oral medicine | % of remaining Compound 5 | |
|---|---|---|
| | Immediately after manufacture | One week after manufacture |
| Control | 87.4 | 33.7 |
| 1 | 100.0 | 100.0 |
| 2 | 100.0 | 100.0 |
| 3 | 100.0 | 100.0 |
| 4 | 100.0 | 100.0 |
| 5 | 100.0 | 100.0 |

PHARMACOLOGICAL EXAMPLE (1) The effect of the compounds of the invention is examined by using aspirin-induced pylorus-ligated rats according to the methods of S. Okabe (Oyo-Yakuri 9 (1), 31–37 1975). The test compounds are given orally at a dose of 500 mg./kg. The obtained ulcer index (mm) and % inhibition of test drugs are shown in Table 2.

TABLE 2

| test compound | dose (mg/kg) | ulcer index (mm) ± S.E. | % inhibition |
|---|---|---|---|
| compound 1 | 500 | 11.0 ± 2.98 | 50.6 |
| compound 2 | 500 | 27.8 ± 7.1 | 35.9 |
| compound 5 | 500 | 2.2 ± 0.8 | 88.1 |
| compound 6 | 500 | 10.3 ± 4.16 | 53.9 |
| compound 11 | 500 | 14.5 ± 5.12 | 33.7 |

(2) The effect on ethanol induced ulcer is examined according to the method of L. Robert (Gastroenterology 77,433–443, 1979) with some modification. Rats are fasted for 24 hrs. and after 30 min. of the oral test drug administration, 1 ml. of 60% ethanol of 150 mM hydrochloric acid solution is given.

Exactly 1 hour later, the animals are sacrificed and the stomach is removed to examine their ulcer index.

The results are shown with % inhibition in Table 3.

TABLE 3

| Test compound | Dose (mg/kg) | ulcer index (mm) | % inhibition |
|---|---|---|---|
| compound 5 | 500 | 3.3 ± 1.2 | 95.1 |
| compound 5 | 100 | 27.1 ± 7.3 | 59.7 |

PHARMACEUTICAL EXAMPLE

The granule composition and injections are as follows.

The parts are by weight unless otherwise specified.

(1) 1 g. of L-arginine and 150 ml of refined water were added to 6 g. of synthesized aluminum silicate and mixed for one hour and distilled out under reduced pressure. Then the resulting residue was crushed and dried for 2-3 hours at 40° C. to obtain the resulting material with the degree of drying to meet the authorized standard.

A powder was obtained after mixing the following composition using said synthesized aluminum silicate subjected to said basic treatment.

| | |
|---|---|
| Compound 5 | 400 mg |
| Basic synthesized aluminum silicate | 309 mg |
| Lactose | 120 mg |
| Avicel | 180 mg |

(2) Instead of synthesized aluminum silicate used in above example 1, 2.0 g of syloid was used and a basic treatment was carried out with 450 mg of L-arginine in a manner similar to example 1 to obtain a powder with the following composition.

| | |
|---|---|
| Compound 5 | 400 mg |
| Basic syloid | 327 mg |
| Lactose | 400 mg |

(3) In place of synthesized aluminum silicate used in example 1, 6.0 g of alcamac was subjected to a basic treatment by the procedure of example 1 and a powder was obtained by mixing the following composition using said treated alcamac.

| | |
|---|---|
| Compound 5 | 400 mg |
| Basic alcamac | 154 mg |
| Lactose | 500 mg |
| Avicel | 180 mg |

(4) In place of synthesized aluminum silicate used in example 1, 2.0 g of neusilin was used and treated with 450 mg of L-arginie and a powder was obtained by mixing the following composition.

| | |
|---|---|
| Compound 5 | 400 mg |
| Basic neusilin | 157 mg |
| Lactose | 550 mg |

(5) 16 ml. of an aqueous solution of 0.1N of NaHCO$_3$ was added to 3 g of synthesized aluminum silicate and the mixture was stirred for one hour. Then the mixture was filtered by suction and the resulting residue was dried for 2-3 hours at 50° C. A powder was obtained under said dried powder by mixing the following composition.

| | |
|---|---|
| Compound 5 | 400 mg |
| Basic synthesized aluminum silicate | 360 mg |
| Lactose | 120 mg |
| Avicel | 180 mg |

(6) The capsule filler composition is compounded from the following ingredients

| | |
|---|---|
| Compound 6 | 30 parts |
| Synthetic hydrotalcite | 24.8 |
| Crystalline cellulose | 5.0 |
| Calcium stearate | 0.2 |

Each capsule contains 150 mg of the mixture.

(7) Injections are compounded from the following ingredients. Each ampul contains 1.0 ml of the solution.

| | |
|---|---|
| compound 5 | 10 parts |
| cotton oil | 30 parts |

SYNTHETIC EXAMPLE 1

2-(4-methyl-3-pentene)-6-methyl-1,3-dioxane (compound 1)

A mixture consisting of 1.2 g. of 5-methyl-4-hexen-1-al, 18 g. of 1,3 butanediol, 0.03 g. of p-toluenesulfonic acid and 30 ml of benzene is refluxed for more than 20 hours, by providing a Dean-Stark trap on a reacting pot.

After cooling, 0.03 g. of sodium acetate is added to the reaction mixture and the reaction mixture is filtered.

After removal of the solvent, the reaction mixture is distilled under reduced pressure giving 0.8 g. of the objective compound at 85° C. (15 mm. Hg).

MS(m/e): 185(M$^+$ +1).

ir: 2950, 2840, 1440, 1420, 1380 cm$^{-1}$.

The compounds from 2 to 14 can be obtained by reacting the compounds in column I of Table 4 with those of column II by the same procedure as mentioned above. Also, physico-chemical data of each compound as shown in Table 4.

TABLE 4

| Compound | I | II | mp | MS (m/c) |
|---|---|---|---|---|
| 2 | CH$_3$C=CH(CH$_2$)$_2$CHCHCHO<br>  \|            \|<br>  CH$_3$     CH$_3$ | HO—CH—CH$_2$CH$_2$OH<br>         \|<br>         CH$_3$ | 91-93°<br>(10 mmHg) | 226 (M$^+$) |
| 3 | CH$_3$—(CH$_2$)$_8$—CHO | " | 110°<br>(3 mmHg) | 228 (M$^+$) |
| 4 | CH$_3$—(CH$_2$)$_2$—CH=CHCHO | " | 85°<br>(10 mmHg) | 169 (M$^+$ − 1) |
| 5 | CH$_3$C=CH—(CH$_2$)$_2$C=O<br>  \|                    \|<br>  CH$_3$              CH$_3$ | " | 85-87°<br>(5 mmHg) | 197 (M$^+$) |
| 6 | CH$_3$—⟨cyclohexanone⟩—CH(CH$_3$)$_2$ | " | 111-113°<br>(3 mmHg) | 227 (M$^+$ + 1) |

TABLE 4-continued

| Compound | I | II | mp | MS (m/c) |
|---|---|---|---|---|
| 7 | CH₃–(C(CH₃)=CHCH₂CH₂)₂CHO | " | 125° (3 mmHg) | 334 (M⁺) |
| 8 | (CH(CH₃)=CHCH₂CH₂)₃–CHO | " | 145–148° (0.3 mmHg) | 265 (M⁺ − 1) |
| 9 | CH₃CH–CH=CHCH₂CH₂CHO (with CH₃ branch) | HO–CH₂–CH₂–CH(CH₃)–OH | 115° (10 mmHg) | 198 (M⁺) |
| 10 | CH₃C(CH₃)–CH(CH₂)₂=C(CH₃)–CH₂CHO | " | 116–118 (4 mmHg) | 240 (M⁺) |
| 11 | CH₃C(CH₃)=CH(CH₂)₂–C(=O)–CH₃ | " | 104° (14 mmHg) | 212 (M⁺) |
| 12 | CH₃–(C(CH₃)=CHCH₂CH₂)₂–C(=O)–CH₃ | " | 108–110 (1.0 mmHg) | 281 (M⁺) |
| 13 | CH–(C(CH₃)=CHCH₂CH₂)₃–C(=O)–CH₃ | " | 153–155 (1.0 mmHg) | 349 (M⁺ + 1) |
| 14 | CH₃–(C(CH₃)=CHCH₂CH₂)₈–C(=O)–CH₃ | HO–CH(CH₃)–CH₂CH₂OH | 125° (0.3 mmHg) | 402 (M⁺) |

What is claimed is:

1. A method of treating peptic ulcer which comprises administering to a patient suffering from peptic ulcer a therapeutic composition comprising a compound of the formula

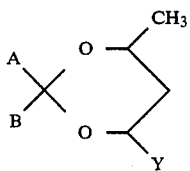

wherein:
A is an alkyl group, an alkenyl group or a

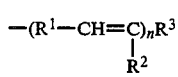

group in which R¹ represents an alkylene group, R² and R³ each represents a hydrogen atom or a lower alkyl group and n is an integer of 1 to 4,
B and Y each represents a hydrogen atom or lower alkyl group, and
A and B together may form a cyclohexyl ring optionally substituted by one or more lower alkyl groups, in an amount effective to inhibit peptic ulcer in combination with a pharmeceutically acceptable carrier.

2. A method of treating peptic ulcer according to claim 1; wherein the carrier contains a pharmaceutically acceptable base sufficient to make the carrier alkaline.

3. A method of treating peptic ulcer according to claim 1; wherein A is said alkenyl group.

4. A method of treating peptic ulcer according to claim 1; wherein A is said

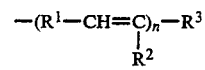

group.

5. A method of treating peptic ulcer according to claim 1; wherein A and B together form a cyclohexyl ring of the formular

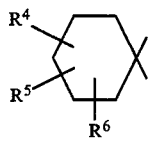

wherein R⁴, R⁵ and R⁶ each represents H or a lower alkyl group.

6. A method of treating peptic ulcer which comprises administering to a patient suffering from peptic ulcer a therapeutic composition comprising a compound having antiulcer activity of the formula

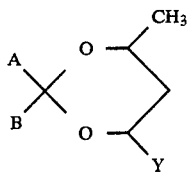

wherein:

A is an alkenyl group or a

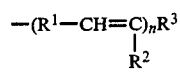

group in which $R^1$ represents an alkylene group, $R^2$ and $R^3$ each represents a hydrogen atom or a lower alkyl group and n is an integer of 1 to 4, and B and Y each represent a hydrogen atom or lower alkyl group, in an amount effective to inhibit peptic ulcer in combination with a pharmaceutically acceptable carrier.

7. A method of treating peptic ulcer according to claim 6; wherein said compound is selected from a member of the group consisting of
2-(4-methyl-3-pentene)-6-methyl-1,3-dioxane,
2-(2-6-dimethyl-6-heptene)-6-methyl-1,3-dioxane,
2-(4-methyl-3-pentenyl)-2-methyl-4-methyl-1,3-dioxane, and
2-(4-methyl-3-pentenyl)-2-methyl-4,6-dimethyl-1,3-dioxane.

* * * * *